(12) United States Patent
Flanders et al.

(10) Patent No.: US 7,482,589 B2
(45) Date of Patent: Jan. 27, 2009

(54) METHOD AND SYSTEM FOR NOISE CONTROL IN SEMICONDUCTOR SPECTROSCOPY SYSTEM

(75) Inventors: Dale C. Flanders, Lexington, MA (US); Walid A. Atia, Lexington, MA (US); Mark E. Kuznetsov, Lexington, MA (US)

(73) Assignee: Axsun Technologies, Inc., Billerica, MA (US)

( * ) Notice: Subject to any disclaimer, the term of this patent is extended or adjusted under 35 U.S.C. 154(b) by 68 days.

(21) Appl. No.: 11/550,503

(22) Filed: Oct. 18, 2006

(65) Prior Publication Data

US 2007/0071040 A1    Mar. 29, 2007

Related U.S. Application Data

(63) Continuation of application No. 10/953,046, filed on Sep. 29, 2004, now Pat. No. 7,157,712.

(51) Int. Cl.
*G01J 5/02* (2006.01)
*H01S 3/10* (2006.01)

(52) U.S. Cl. ..................................... 250/339.07; 372/20

(58) Field of Classification Search ............ 250/339.07, 250/339.06, 339.01, 339.11; 372/20, 32
See application file for complete search history.

(56) References Cited

U.S. PATENT DOCUMENTS

| | | | |
|---|---|---|---|
| 5,039,855 A | 8/1991 | Kemeny et al. | |
| 5,450,428 A | 9/1995 | Maeda | |
| 5,475,221 A | 12/1995 | Wang | |
| 5,668,659 A | 9/1997 | Sakamoto et al. | |
| 5,867,512 A | 2/1999 | Sacher | |
| 6,160,826 A | 12/2000 | Swanson et al. | |

(Continued)

FOREIGN PATENT DOCUMENTS

EP     1 059 712 A2     12/2000

(Continued)

OTHER PUBLICATIONS

International Preliminary Report on Patentability from International Application No. PCT/US2005/033712, filed Sep. 20, 2005.

(Continued)

*Primary Examiner*—David P Porta
*Assistant Examiner*—Faye Boosalis
(74) *Attorney, Agent, or Firm*—Houston Eliseeva LLP

(57) ABSTRACT

An optical power control system for a semiconductor source spectroscopy system controls power fluctuations in the tunable signal from the spectroscopy system and thus improves the noise performance of the system. This general solution has advantages relative to other systems that simply detect reference power levels during the scan and then correct the detected signal after interaction with the sample by reducing the requirements for coordinating the operation of the sample detectors and power or reference detectors. The spectroscopy system comprises a semiconductor source and a tunable filter. The combination of the semiconductor source and tunable signal illuminate a sample with a tunable signal, being tunable over a scan band. The power control system comprises an amplitude detector system for detecting the power of the tunable optical signal and power control system for regulating the amplitude of the tunable optical signal in response to its detected power.

19 Claims, 16 Drawing Sheets

U.S. PATENT DOCUMENTS

| | | |
|---|---|---|
| 6,339,603 B1 | 1/2002 | Flanders et al. |
| 6,373,632 B1 | 4/2002 | Flanders |
| 6,490,074 B1 | 12/2002 | Korn |
| 6,661,814 B1 | 12/2003 | Chapman et al. |
| 6,731,661 B2 | 5/2004 | Trutna, Jr. |
| 6,924,928 B2 | 8/2005 | Dennis et al. |
| 2001/0036206 A1 | 11/2001 | Jerman et al. |
| 2002/0136104 A1 | 9/2002 | Daiber |
| 2002/0163942 A1 | 11/2002 | Baillargeon et al. |
| 2003/0020926 A1 | 1/2003 | Miron |
| 2003/0026302 A1 | 2/2003 | Anthon et al. |
| 2005/0098713 A1* | 5/2005 | Holland .................... 250/221 |
| 2006/0124852 A1* | 6/2006 | Von Drasek ........... 250/339.13 |

FOREIGN PATENT DOCUMENTS

| | | |
|---|---|---|
| WO | 2005/038418 A2 | 4/2005 |

OTHER PUBLICATIONS

Sidorin, Yakov, et al., "Demostration of a Tunable Hybrid Laser Diode Using an Electrostatically Tunable Silicon Micromachined Fabry-Perot Interferometer Device," IEEE Photonics Technlogy Letters, vol. 11, No. 1, Jan. 1999, pp. 18-20, XP-000801378.

Krawczyk, Stanislas K., et al., "GaN and Related Compounds for MEMS and MOEMS," Aromagraph DC 3000 System, vol. 41, No. 8, Aug. 1999, pp. 622-625, XP-001058333.

Innolight Diabolo Product Line Brochure, "When Stability Matters, Ultrastable, CE, Single-Frequency Lasers in the Visible Spectral Region," Innolight, Hannover, Germany, Feb. 2003, 4 pp.

InfraPrime Lab Brochure, "The profit centre for your laboratory," http://www.barn-luebbe.de.deu/__ tempshort/analytics_web/en/infraprime.html, Jun. 30, 2003, 3pp.

Quantum Technology, Inc. data sheet, Model 307A, Noise Eater, data sheet 723, Quantum Technology, Inc., Florida, http://www.quantumtech.com, May 2002, 2 pp.

International Search Report from International application No. PCT/US2005/033712, filed Sep. 20, 2005.

\* cited by examiner

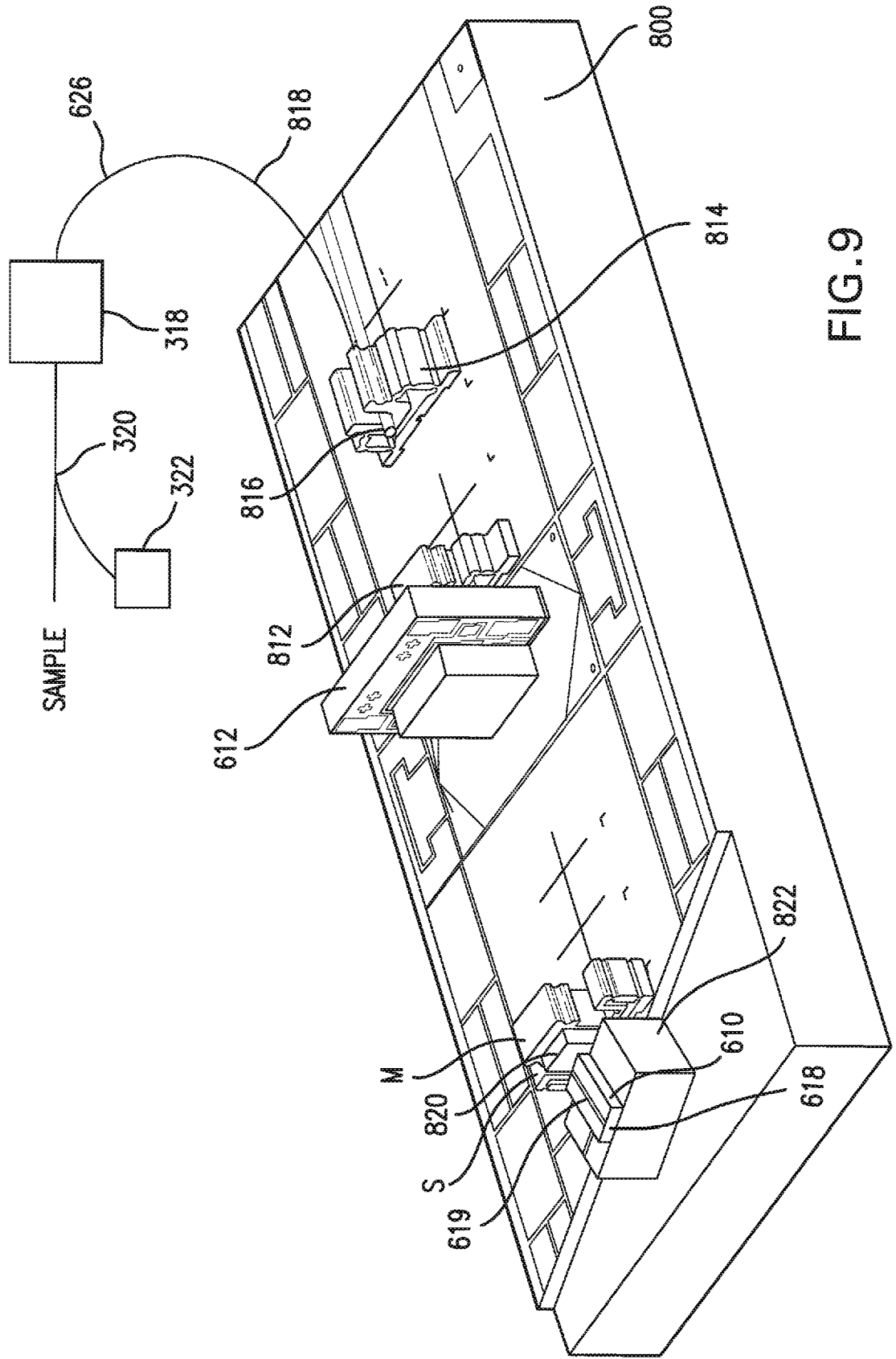

US 7,482,589 B2

METHOD AND SYSTEM FOR NOISE CONTROL IN SEMICONDUCTOR SPECTROSCOPY SYSTEM

RELATED APPLICATIONS

This application is a continuation of copending U.S. application Ser. No. 10/953,046 filed on Sep. 29, 2004 and published as U.S. Publication No. U.S. 2006/0065834-A1, which is related to application Ser. Nos. 10/953,048, published as U.S. Publication No. U.S. 2006/0072633 A1, and 10/953,043, published as U.S. Publication No. U.S. 2006/0072632 A1, both filed on Sept. 29, 2004, by Flanders, et al., which are incorporated herein by this reference.

BACKGROUND OF THE INVENTION

Most spectroscopy systems fall into one of two categories. They can be tunable source systems that generate a tunable optical signal that is scanned over a scan band. A detector is then used to detect the tunable optical signal after interaction with the sample. The time response of the detector corresponds to the spectral response of the sample. Such systems are typically referred to as pre-dispersive. Alternatively, a tunable detector system can be used. In this case, a broadband signal is used to illuminate the sample. Then, a bandpass filter is tuned over the scan band such that a detector time response is used to resolve the sample's spectrum. Such systems are typically referred to as post-dispersive.

Among tunable source and tunable detector systems, tunable source systems have some advantages. They can have a better response for the same optical power transmitted to the sample. That is, tunable detector systems must illuminate the sample with a broadband power signal that covers the entire scan band. Sometimes, this can result in excessive sample heating. Also high power is generated at the optical source, most of it being unused, making the system inefficient. In contrast, at any given instant, tunable source systems only generate and illuminate the sample with a very narrow band power within the scan band.

Further, tunable source systems have advantages associated with detection efficiency. Relatively large detectors can be used to capture a larger fraction of the light that may have been scattered by the sample, since there is no need to capture light and then collimate the light for transmission through a tunable filter or to a grating and a detector array.

A number of general configurations are used for tunable source spectroscopy systems. The lasers have advantages in that very intense tunable optical signals can be generated. A different configuration uses the combination of a broadband source and a tunable passband filter, which generates the narrowband signal that illuminates the sample.

Historically, most tunable lasers were based on solid state or liquid dye gain media. While often powerful, these systems also have high power consumptions. Tunable semiconductor laser systems have the advantage of relying on small, efficient, and robust semiconductor sources. One configuration uses semiconductor optical amplifiers (SOAs) and microelectromechanical system (MEMS) Fabry-Perot tunable filters, as described in U.S. Pat. No. 6,339,603, by Flanders, et al., which is incorporated herein by this reference in its entirety.

In commercial examples of the broadband source/tunable filter source configuration, the tunable filter is an acousto-optic tunable filter (AOTF) and the broadband signal is generated by a diode array or tungsten-halogen bulb, for example. More recently, some of the present inventors have proposed a tunable source that combines edge-emitting, superluminescent light emitting diodes (SLEDs) and MEMS Fabry-Perot tunable filters to generate the tunable optical signal. See U.S. Pat. appl. Publication No. US 2005-0083533 A1 published on Apr. 21, 2005, now U.S. Pat. No. 7,061,618, issued on Jun. 13, 2006, by Atia, et at., which is incorporated herein by this reference in its entirety. The MEMS device is highly stable and can handle high optical powers and can further be much smaller and more energy-efficient than typically large and expensive AOTFs. Moreover, the SLEDS can generate very intense broadband optical signals over large bandwidths, having a much greater spectral brightness than tungsten-halogen sources, for example.

SUMMARY OF THE INVENTION

One drawback associated with semiconductor spectroscopy systems, however, is noise. Examples are shot noise, thermal noise, and relative intensity noise or RIN. Shot noise is generated by random fluctuations of current flowing through the detector due to the quantum nature of charge. Thermal noise results from electrons being freed in the detector due to thermal vibration and being indistinguishable from photoelectrons. RIN results from quantum fluctuations in the generation of light in the semiconductor cavity, being caused by optical interference between the signal and spontaneous emission within the cavity or changes in how the optical energy is instantaneously partitioned over the scan band. At higher optical powers, RIN dictates overall performance or signal-to-ratio (SNR), whereas at lower optical powers, shot noise usually tends to restrict the performance of the system.

RIN, however, is not unique to semiconductor sources. It can impact the performance of solid state laser spectroscopy systems as well as systems based on tungsten-halogen bulbs or standard diodes. But, it tends to be larger in semiconductor sources, such as optically filtered SLEDS and SOAs. Thus, while semiconductor sources provide advantages such as long life, high spectral brightness, size, and efficiency, on one hand, they tend to have somewhat worse inherent noise characteristics, on the other.

The present invention is directed to an optical power control system for a semiconductor source spectroscopy system. As such, this optical power control system can be used to control power fluctuations in the tunable signal from the spectroscopy system and thus improve the noise performance of the system.

This general solution has advantages relative to other systems that simply detect reference power levels during the scan and then correct the detected signal after interaction with the sample, since this solution reduces requirements for coordinating the operation of the sample detectors and power or reference detectors.

In general, according to one aspect, the invention features an optical power control system for a semiconductor source spectroscopy system. This spectroscopy system comprises a semiconductor source and a tunable filter. The combination of the semiconductor source and tunable filter illuminate a sample with a tunable signal, being tunable over a scan band. A detector is provided for detecting a sample signal generated by the interaction of the tunable signal with the sample.

The power control system comprises an amplitude detector system for detecting the power of the tunable optical signal and a power control system for regulating the amplitude of the tunable optical signal in response to its detected power.

In one embodiment, the semiconductor source comprises a light emitting diode generating a broadband signal that is converted to the tunable, narrowband signal by the tunable filter. In some implementations, standard light emitting diodes can be used. In other examples, superluminescent light emitting diodes are used. These are edge-emitting devices that can generate high power broadband signals. In fact, SLED's are currently preferred because of their high spectral brightness.

In another example, the semiconductor spectroscopy system comprises a rare-earth-doped gain fiber, such as an erbium-doped fiber, which is optically pumped by at least one semiconductor diode laser.

In some embodiments, the semiconductor source spectroscopy system comprises a laser cavity. In this case, the semiconductor source is a semiconductor optical amplifier. In some implementations, both facets of the SOA chip are coated to be anti-reflective. However, in other examples, a reflective SOA is used such that one end of the SOA defines one end of the laser cavity. The tunable filter is located within the laser cavity in order to provide a tunable laser configuration. In one implementation, the laser cavity is a linear cavity. However, in other cases, a ring laser configuration is used.

In the preferred embodiment, the tunable filter is a micro-electro mechanical (MEMS) filter. In one implementation, this MEMS filter comprises two thin film dielectric mirror structures providing for a low loss, high finesse system that can provide efficient, narrow bandwidth operation.

In the preferred embodiment, the amplitude detector system comprises a detector and a tap providing a portion of the tunable signal to the detector. In the current preferred embodiment, the semiconductor source, tunable optical filter, amplitude detector, and tap are attached to a common optical bench. It provides a small, highly integrated, highly stable, and highly mechanically robust system. In another embodiment, the optical tap and detector are in a separate package from the semiconductor-filter tunable light source.

The power control system then regulates the amplitude of the tunable optical signal in response to the amplitude detector. In one embodiment, the power control system regulates the amplitude of the tunable optical signal by controlling the power or current to the semiconductor source. However, in a different embodiment, a separate optical signal power regulator is provided to modulate the power of the tunable optical signal. This can be achieved with a semiconductor optical amplifier, for example. In the preferred implementation, however, a variable attenuator is used to dynamically attenuate the tunable signal in order to stabilize its output power across the scan band. Further, a combination of current control and optical signal power regulator are used in still other implementations.

Finally, in some implementations, a frequency reference system is further provided for detecting an instantaneous frequency of the tunable optical signal in order to further improve its performance and spectral accuracy. In one embodiment, for example, the amplitude detector system and frequency reference system are attached to a common optical bench.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 7A-1 is a block diagram showing the operation of the inventive drive circuit;

FIG. 9 is a perspective view of a linear cavity tunable laser according o the present invention;

DETAILED DESCRIPTION OF THE PREFERRED EMBODIMENTS

Figure 1:
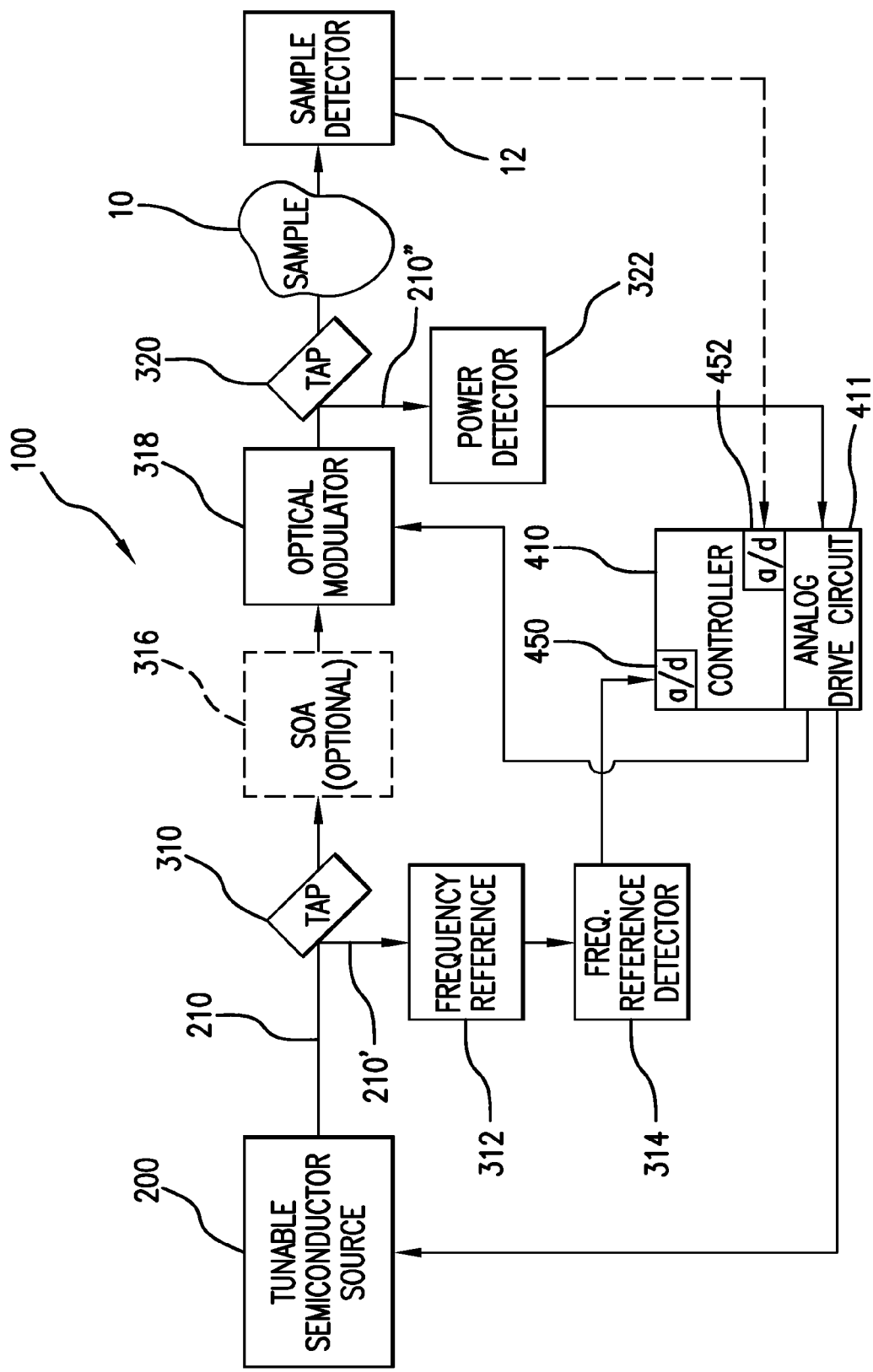
FIG. 1 is a perspective view of a tunable source semiconductor spectroscopy system with a wavelength and amplitude referencing system according to the present invention.

FIG. 1 shows a semiconductor source spectroscopy system 100, which has been constructed according to the principles of the present invention.

Generally, the spectroscopy system 100 comprises a tunable semiconductor source 200. This generates a tunable optical signal 210.

In one example, the tunable signal 210 is transmitted to a frequency reference tap 310 that diverts a portion of the tunable optical signal 210' to an optical frequency or wavelength reference 312. In one example, this optical reference is a fixed cavity etalon that provides a number of spectral passbands located within and/or spectrally adjacent the scan band of the system 100. Optionally, a post-amplifier tracking tunable optical filter is sometimes used to filter out or remove any optical noise contributed by the amplifier.

The signal 210' that is transmitted through the optical reference 312 is then detected by a frequency reference detector 314. The output of the frequency reference detector 314 is sent to an analog to digital converter 450 of a controller 410. This enables the controller 410 to determine the instantaneous frequency of the tunable signal 210 to thereby provide frequency or wavelength calibration for the spectroscopy system 100.

In some implementations, the tunable optical signal 210 is then amplified in an optical amplifier 316. In one example, this optical amplifier can be a rare-earth doped amplifier, such as a fiber amplifier or waveguide amplifier. In a more preferable embodiment, a semiconductor optical amplifier is used to boost or increase the power of the tunable optical signal 210 while not significantly increasing the overall size of the system 100.

The tunable optical signal 210 is then transmitted to an optical signal power regulator 318 of the power control system. This modulates the power of the tunable optical signal 210.

In one example, the optical signal power regulator comprises an SOA that selectively amplifies or attenuates the tunable optical signal 210 by control of the SOA drive current. In this example, the optional SOA amplifier 316 would usually not be used.

In the preferred embodiment, the optical signal regulator or modulator 318 is a variable optical signal attenuator. Preferably, it is a solid state, high-speed optical attenuator. One commercial example is available from Boston Applied Technologies, Inc. These are electro-optical, ceramic devices that are electrically modulated in order to control the level of the optical attenuation applied by the regulator 318 to the tunable signal 210.

The power detector 322 detects the amplitude of the tunable optical signal from the optical signal regulator 318. Specifically, a portion 210" of the tunable optical signal 210 is preferably diverted by a power tap 320 to a power detector 322 of the power control system. The detected level of the tunable signal 210 is then provided to the controller 410, and specifically its drive circuit 411.

The remainder of the tunable optical signal 210 is sent through to the sample 10 and the sample detector 12. In some examples, the output of this sample detector 12 is also provided to the controller 410, which is then able to resolve the spectrum of the sample 10 by resolving the time response of the sample detector 12 into the spectral response of the sample 10.

The drive circuit 411 of the controller 410 is used to regulate the power to the tunable semiconductor source 200 or the optical signal regulator 318, or both. Specifically, the output of the power detector 322 provides a power feedback signal that the drive circuit 411 of the controller 410 uses in order to stabilize the level and reduce amplitude noise of the tunable signal 210 in spite of noise such as RIN noise or mode-hopping noise. The controller drive circuit 411 regulates the tunable semiconductor source 200 and/or optical signal attenuator 318 in order to stabilize or set the power in the tunable optical signal 210 over the scan band.

FIGS. 2A-2D show a number of examples of the tunable semiconductor sources 200 that are used in embodiments of the inventive spectroscopy system 100.

Figure 2D:
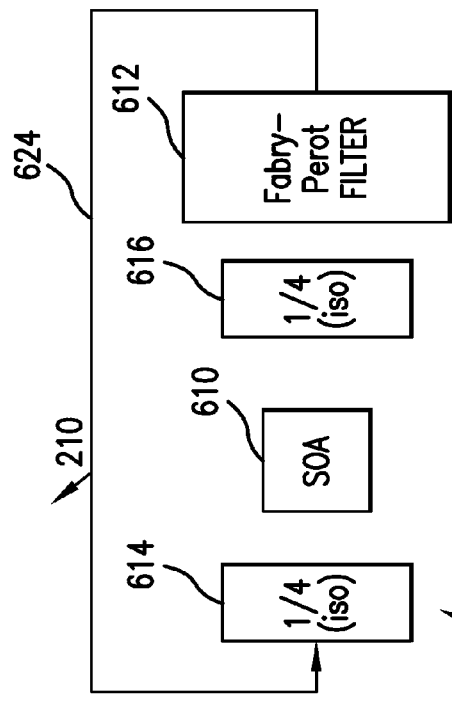
FIGS. 2A through 2D illustrate a number of examples of the tunable semiconductor source for use with the present invention.
Figure 2A:
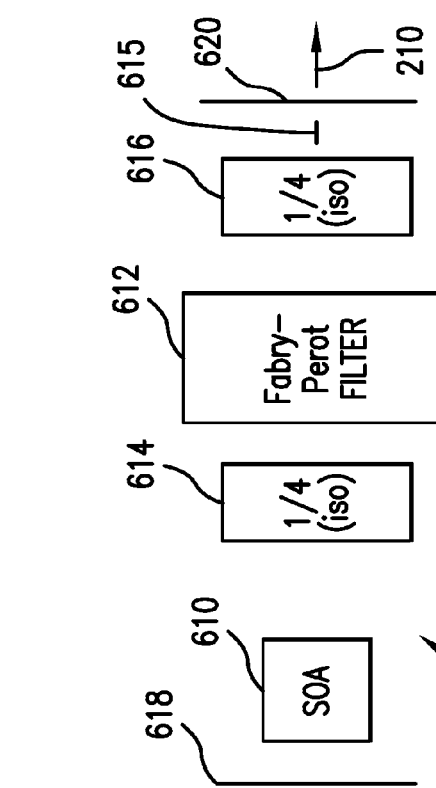

Specifically, FIG. 2A shows a first linear cavity laser embodiment (200-1) of the tunable semiconductor source 200. This is generally analogous to the tunable laser described in incorporated U.S. Pat. No. 6,339,603.

Specifically, light is amplified in an SOA 610. This light is filtered by an intracavity Fabry-Perot tunable filter 612. In one embodiment, the Fabry-Perot tunable filter is manufactured as described in U.S. Pat. No. 6,608,711 or 6,373,632, which are incorporated herein by this reference.

Out-of-band reflections from the filter 612 are isolated from being amplified in the SOA 610 by a first isolation element 614 and a second isolation element 616, on either side of the filter 612 in the optical train. In different implementations, these isolation elements 614, 616 are isolators or quarterwave plates. The laser cavity is defined by a first mirror 618 and a second mirror 620. In some implementations, a reflective SOA 610 is used, which provides the reflectivity of the first mirror 618 at one end of the cavity. The tunable signal 210 is emitted through the second mirror 620 in one example.

In some embodiments, a portion of the laser cavity includes a length of optical fiber 615. The second mirror 620 is then typically a discrete mirror or a fiber Bragg grating reflector that is formed in the fiber 615. The advantage of using the hybrid freespace/fiber laser cavity is that the laser cavity can be made long, typically longer than 10 centimeters, and preferably long than 0.5 meters. The long cavity provides for tight longitudinal mode spacing to reduce mode hopping noise.

In a current embodiment, the SOA chip 610 is polarization anisotropic. Thus, polarization control is desired to stabilize its operation. As such, fiber 615 is polarization controlling fiber such a polarization maintaining or is fiber that only transmits or propagates a single polarization.

Figure 2C:
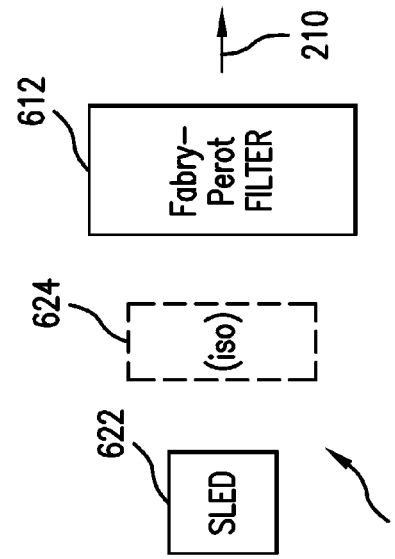
Figure 2B:
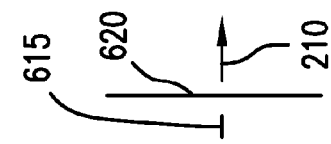
Figure 2B:
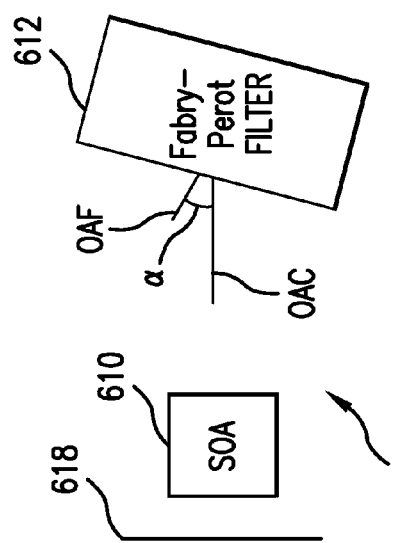

FIG. 2B shows another implementation (200-2) of the linear cavity tunable laser functioning as the tunable semiconductor source 200. Here, an SOA 610 is used in combination with a first mirror 618 and a second mirror 620. The SOA 610 is isolated from the out of passband reflection of the Fabry-Perot tunable filter 612 by tilt isolation. Typically the angle a between the optical axis OAF of the filter 612 and the optical axis of the laser cavity OAC is less than 5 degrees, and preferably between 1 and 3 degrees. Currently, angle $\alpha$ is about 1.3 degrees. In this way, the system avoids the out-of-band reflections from being amplified in the SOA 610. Preferably the tunable filter 612 has flat-flat mirror cavity to further improve isolation.

In this embodiment, a hybrid freespace-fiber cavity is used in some implementations to provide the long optical cavity/tight mode spacing characteristics by further including the fiber length 615.

In a current embodiment, the SOA chip 610 is again polarization anisotropic. Thus, polarization control is desired to stabilize its operation. As such, fiber 615 is polarization controlling fiber such a polarization maintaining or is fiber that only transmits or propagates a single polarization.

FIG. 2C shows another implementation (200-3) of the tunable semiconductor source. Here, a SLED 622 is used to generate a broadband signal that is then filtered by a Fabry-Perot tunable filter 612 in order to generate the tunable signal 210. In other implementations, an intervening isolator 624 or tilt isolation is used to isolate the SLED 622 from he back reflection of the Fabry-Perot tunable filter 612. Further, incorporated U.S. Pat. appl. Publication No. US 2005-0083533 A1 published on Apr. 21, 2005, now U.S. Pat. No. 7,061,618, issued on Jun. 13, 2006 by Atia, et at., describes some other variants, which are used in still other embodiments, depending on whether increased scan band or power is required.

Finally, FIG. 2D shows another implementation (200-4) of the tunable semiconductor source 200. This also combines an SOA 610 and a Fabry-Perot filter 612. A ring cavity laser, however, is used. Specifically an optical fiber or bent beam path 626 is used to recirculate the light back through the SOA 610 for further amplification.

Figure 3:
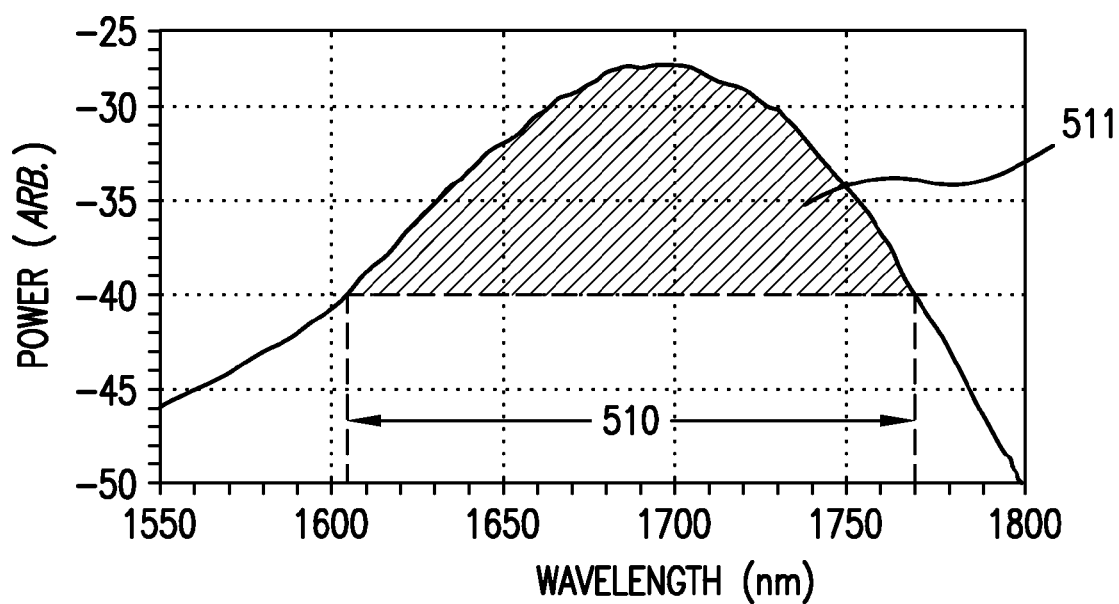
FIG. 3 is a plot of power (decibel scale) showing the gain spectrum of a semiconductor source as a function of wavelength.

FIG. 3 is a plot of the power (arbitrary units, decibels) for a SLED or SOA as a function of wavelength in nanometers, which applies to the various embodiments of the semiconductor tunable source 200 in FIGS. 2A-2D. This plot shows how the power output from the system is stabilized across the scan band.

Generally, the unmodulated SLED or SOA power spectrum will peak at some wavelength, here approximately 1680 nanometers (nm). This wavelength is usually dictated by the epitaxial structure of the devices along with the material system that is used. The power, however, can vary by greater than −40 dB over the desired scan band 510, extending from about 1610 nm to 1770 nm, in this one example. This is due to the fact that the semiconductor gain medium does not generate all wavelengths within the scan band with equal efficiency. Moreover, the power in a narrow slice of the spectrum varies over time due to thermal noise and RIN.

The power to the tunable semiconductor source 200 and/or the optical signal regulator 318 are preferably controlled to stabilize the power of the tunable signal 210 transmitted to the sample from the semiconductor source 200 so that it is stable or at least known across the entire scan band of approximately 1610 to 1770 nm, in one exemplary scan band. In this way, the rolloff in the power spectrum is compensated. As a result, where an attenuator optical power regulator is used or the power to the SLED/SOA is modulated, the tunable optical signal power is attenuated or the power from the semiconductor source is lowered in order to achieve a stable or constant tunable signal power. However, the total power from the system 100 is lower than it would be otherwise be capable of generating, see area 511. In this way, the present system can be used to stabilize the output power of the source due to spectral roll-off associated with limitations in the gain band of the semiconductor sources.

Figure 4:
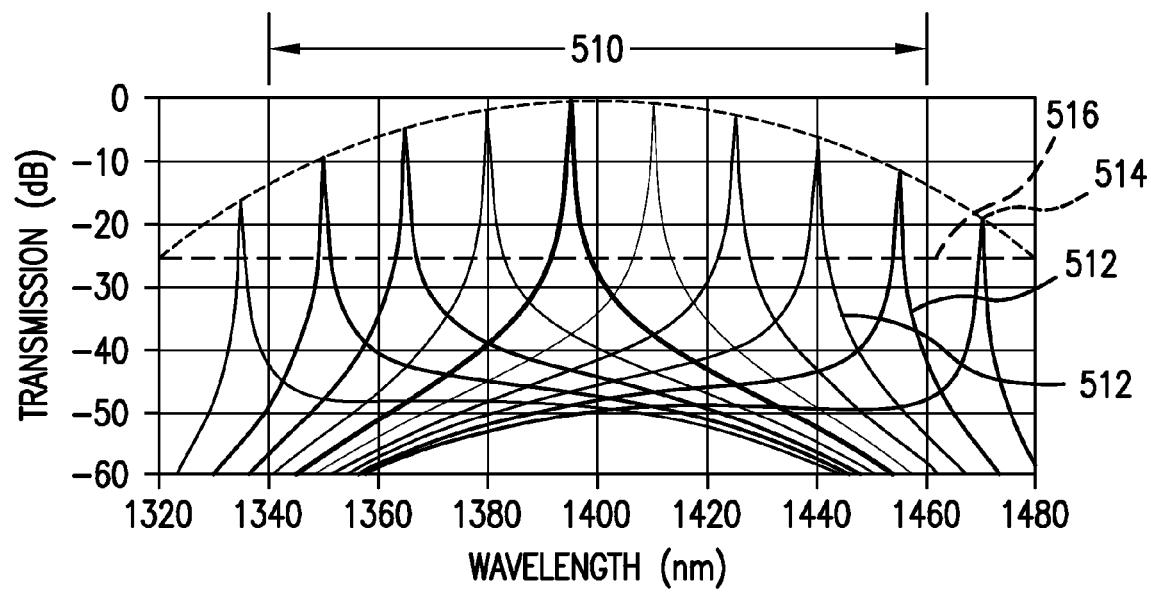
FIG. 4 is a plot of transmission (decibel scale) showing the gain spectrum of the semiconductor source and the passband of the tunable filter.

FIG. 4 is a plot of several tunable filter passbands 512 as a function of an exemplary SLED or SOA power spectrum 514 over a scan band 510 stretching from approximately 1340 to 1460 nm. This plot shows the relationship between the tunable passband of the Fabry-Perot tunable filter 612, the semiconductor source gain spectrum 514, and the operation of the inventive power control system.

As a result, without modulating the power of the tunable optical signal, the output power filling the passband 512 of the tunable filter 612 would peak at about 1400 nm. However, by modulating the power to the SLED 622 or SOA 610 or by controlling its attenuation using optical signal modulator 318, the output power can be stabilized to the level 516. Moreover, by modulating the tunable signal power at high speed, temporal amplitude fluctuations in the tunable signal 210 are mitigated or removed. This has the effect of increasing the SNR of the system and reducing the noise power over the scan band.

Figure 5A:
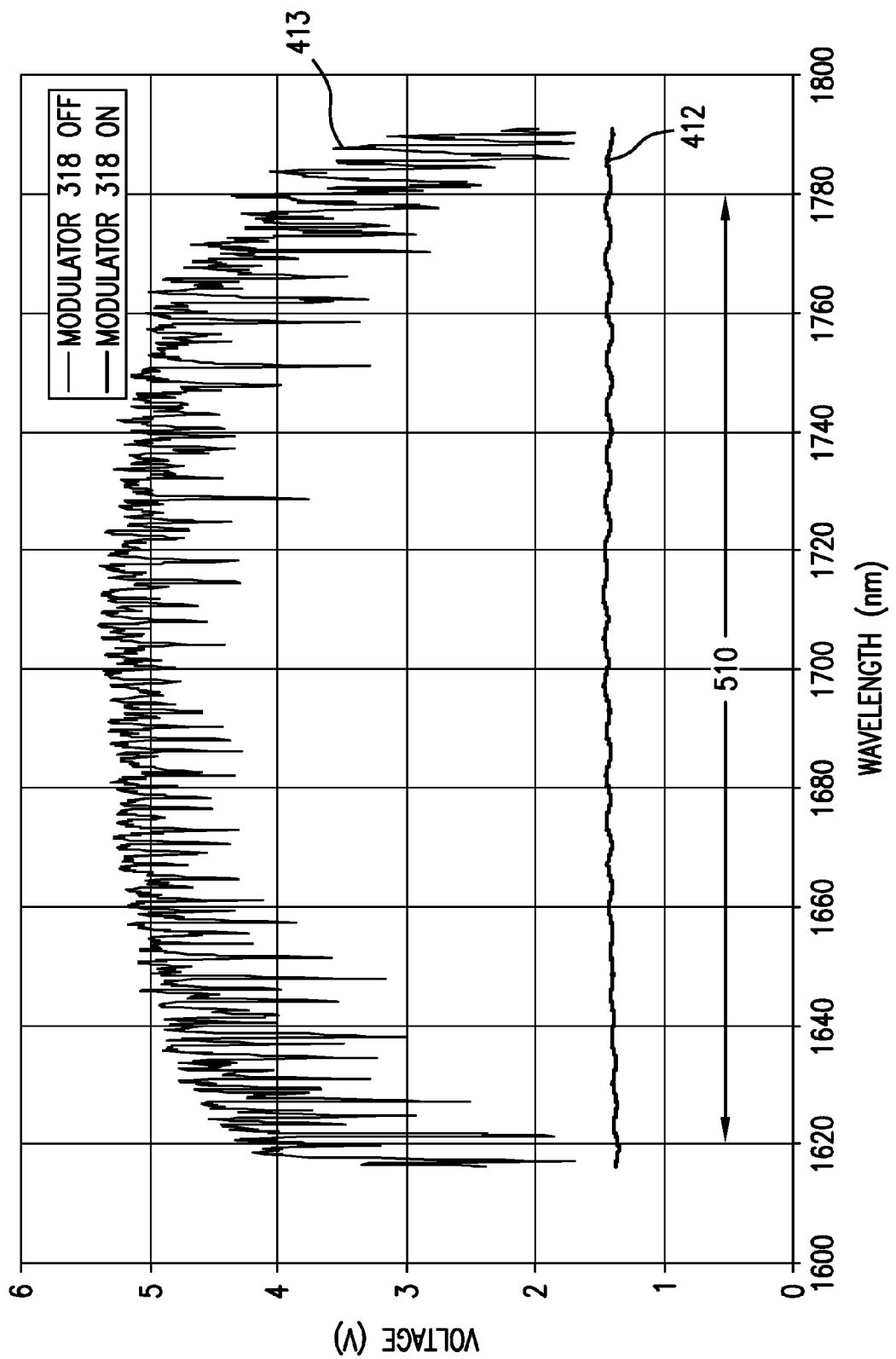
FIG. 5A is a plot of signal optical power as a function wavelength for a semiconductor source using the inventive spectral rolloff compensation and noise suppression.

FIG. 5A is a plot of the response of the power detector 322 as a function of the wavelength across the scan band of semiconductor spectroscopy system 100 showing the performance improvement provided by the present invention.

These data were taken from the embodiment that used the modulation of the optical signal attenuator 318 in order to improve the noise performance of the system.

Specifically, plot 413 shows the response at the sample detector 12 with the attenuator 318 not being driven, i.e., in a transmissive state. No sample 10 is present for this experiment. The spectrum generally peaks around 1,700 nm, which is the center of the gain band of the semiconductor source 610. Further, the power exhibits a high degree of variability across the scan band 510.

In contrast, data 412 illustrate the response at the sample detector 322 with the attenuator 318 being driven by drive circuit 411 in order to flatten the response. Specifically, the response is generally flat across an entire scan band from approximately 1620 to 1780 nm, showing only a small degree of ripple, which is believed to be attributable to polarization sensitivity in one of the taps. Most importantly, the high frequency variability has been reduced, improving the noise performance of the system.

Of note is the fact that the power output from the system is generally lower when the attenuator 318 is in operation. This is because it achieves the spectral flatness and stability by selectively attenuating the tunable optical signal 210.

Figure 5B:
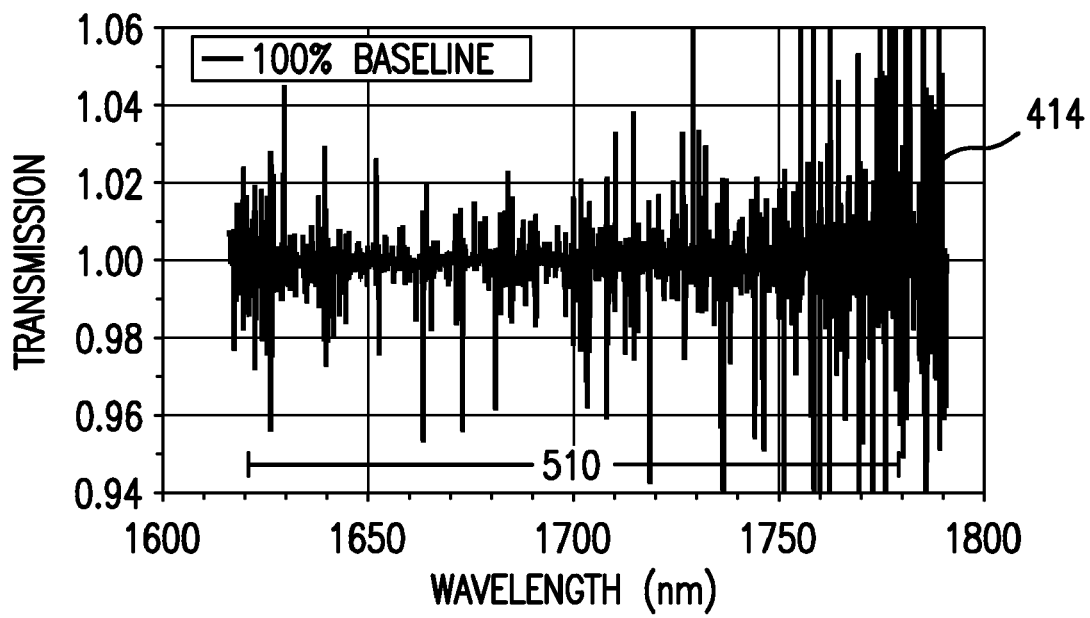
FIG. 5B is a plot of transmission noise as a function wavelength for a semiconductor source using the inventive noise suppression system.
Figure 5C:
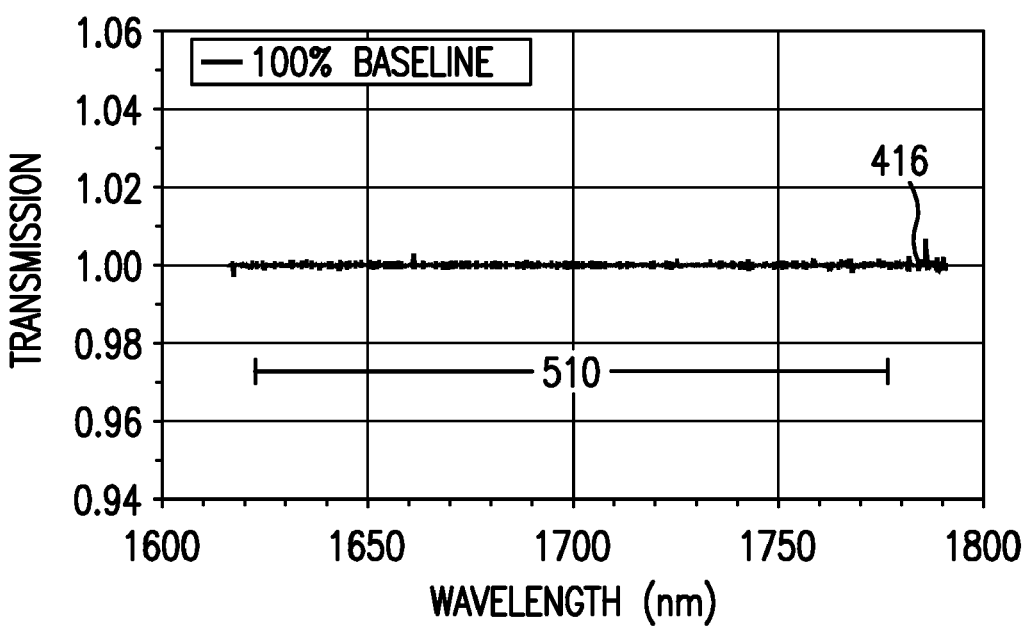
FIG. 5C is a plot of transmission noise as a function wavelength for a semiconductor source using the inventive noise suppression system.

FIG. 5B is a plot of transmission as a function of wavelength across the scan band. Here again, the response with the attenuator not operating is shown by data 414. However, when the attenuator is being driven to stabilize the output, the transmission 416 stabilizes around the normalized value of 1.

Figure 6:
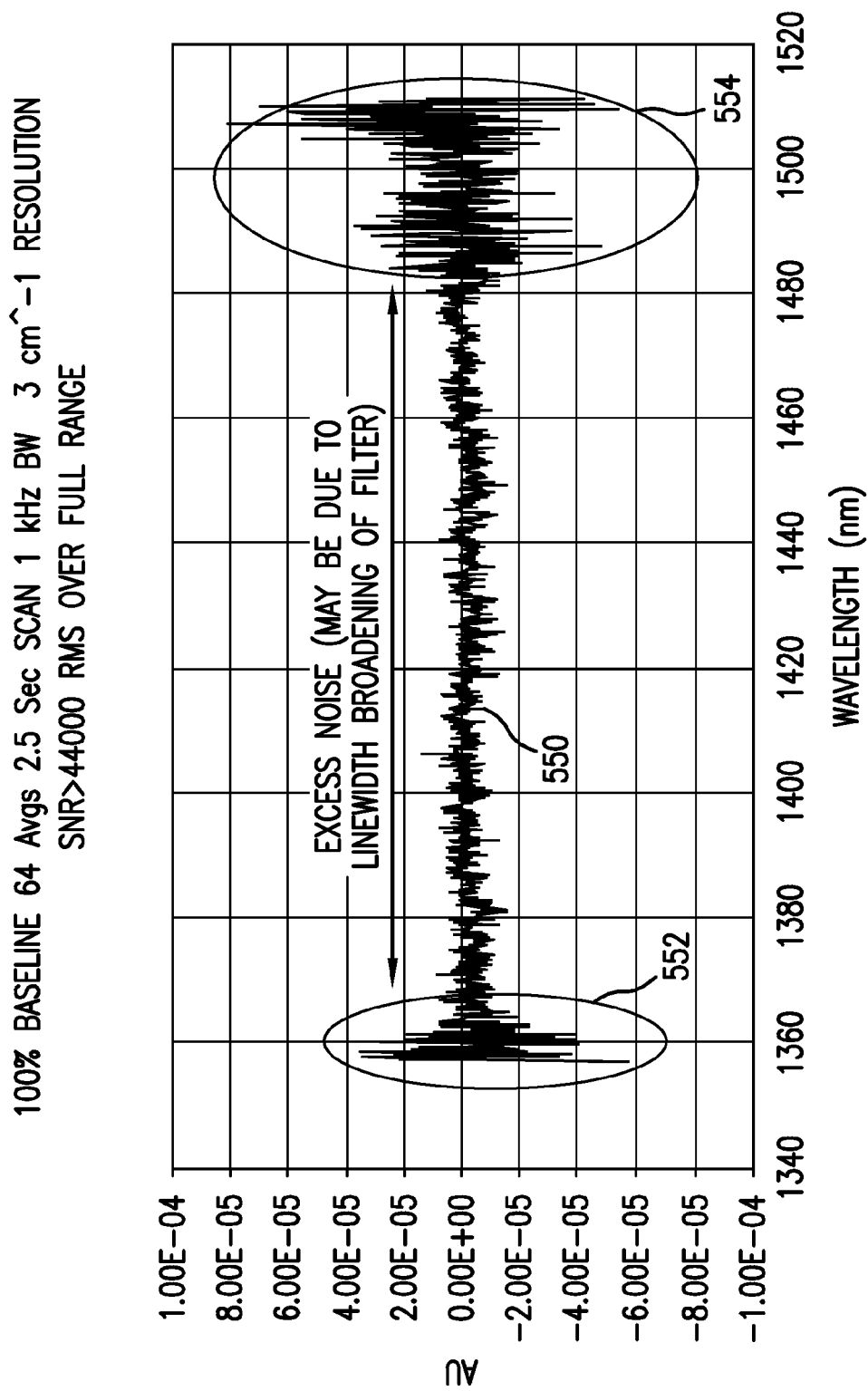
FIG. 6 is a plot of noise as a function of wavelength showing the noise suppression gained from current control of the semiconductor chip.

FIG. 6 is a plot of the response of the sample detector 12 as a function of the wavelength across the scan band of semiconductor spectroscopy system 100 showing the performance improvement provided by the present invention by using current control to the semiconductor SOA chip 610 or SLED chip 622 in order to improve the noise performance of the system.

Specifically, plot 550 shows the normalized transmission response at the sample detector 12 in absorbance units (absorbance $=Log_{10}(transmission^{-1})$). The spectral noise has been substantially reduced. In the illustrated example, the SNR was greater than 44000 RMS. However, the noise performance did degrade in regions 552 and 554, possibly due to a broadening of the tunable filter's passband in these spectral regions.

Figure 7A:
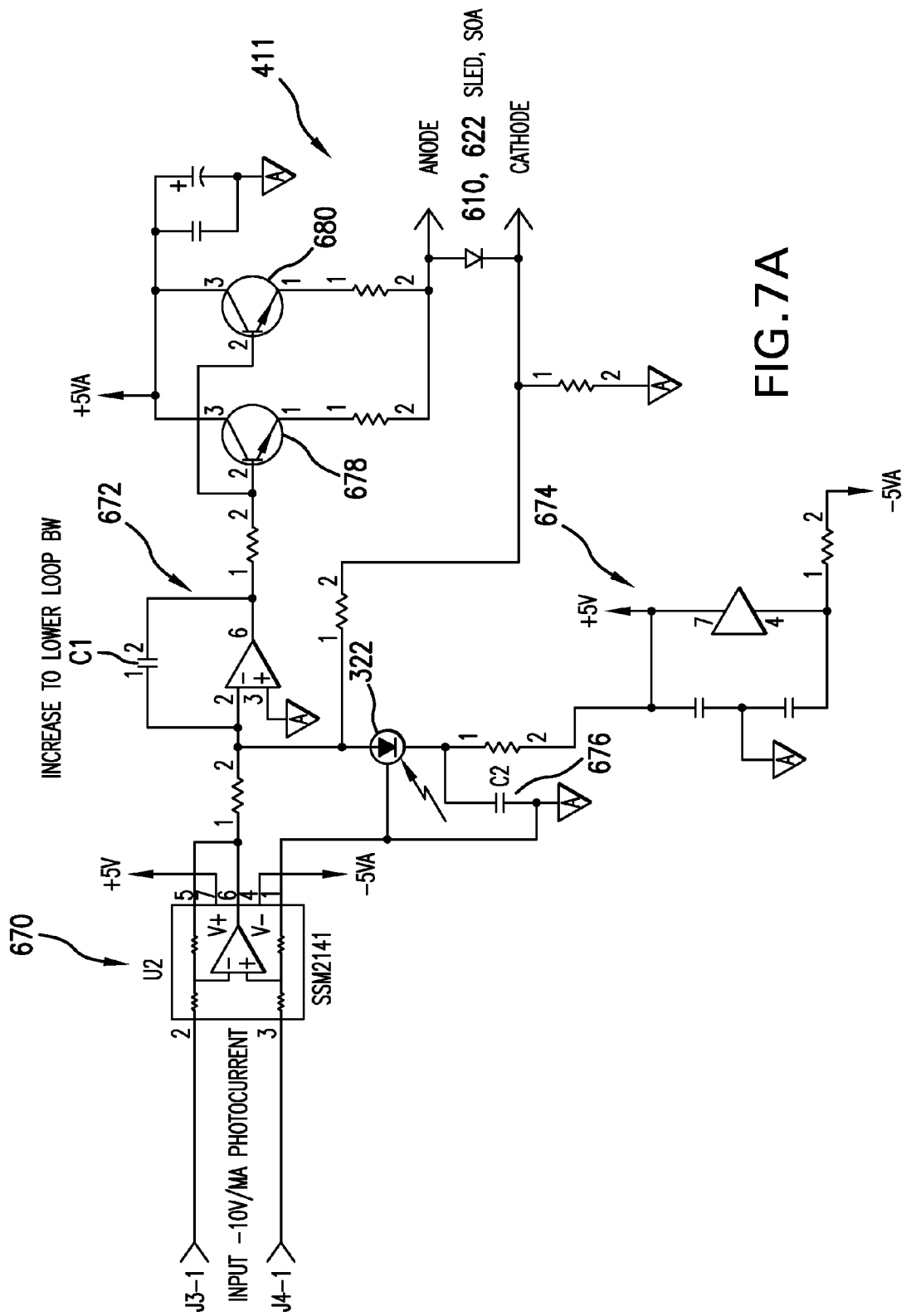
FIG. 7A is a circuit diagram showing an inventive analog drive circuit for the semiconductor source.
Figures 1, 7A:
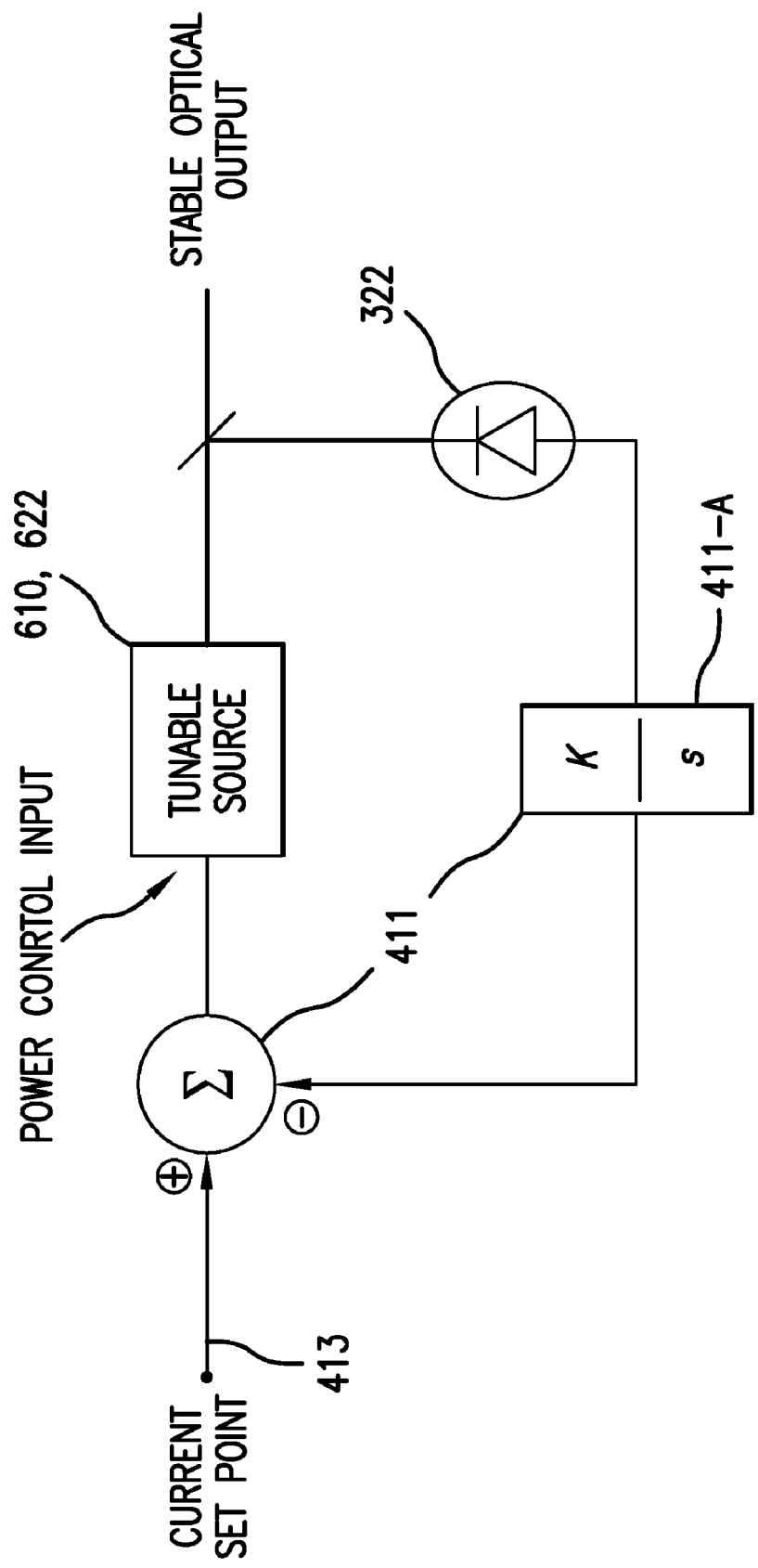

FIG. 7A is a circuit diagram showing the semiconductor source drive circuit 411. This is used in the embodiments that control the current to the SLED 622 or SOA 610 in order to achieve a power-stable tunable signal 210.

The circuit comprises a transimpedance amplifier 670. This element is not always necessary. In the current embodiment, it is used for common mode rejection of noise sources, such as 60 hertz interference.

The voltage across the power detector photodiode 322 regulates the input to an integrating amplifier 672. Specifically, integrating amplifier 672 is used to control the loop bandwidth. By changing capacitor C 1, the bandwidth response of the circuit can be adjusted.

Sub-circuit 674 is used to control the biasing of the photodiode 322. Capacitor C2 (reference numeral 676) controls the frequency response of the circuit.

In the illustrated embodiment, two power transistors 678 and 680 are used to control the power to the anode of the SLED 622 or SOA 610.

FIG. 7A-1 is a block diagram illustrating the operation of the drive circuit 411. Specifically detector 322 provides the feedback signal to drive circuit 411. The drive circuit signal is then summed with a current set point signal 413. This is the power control signal to the SOA or SLED 610, 622.

Figure 7B:
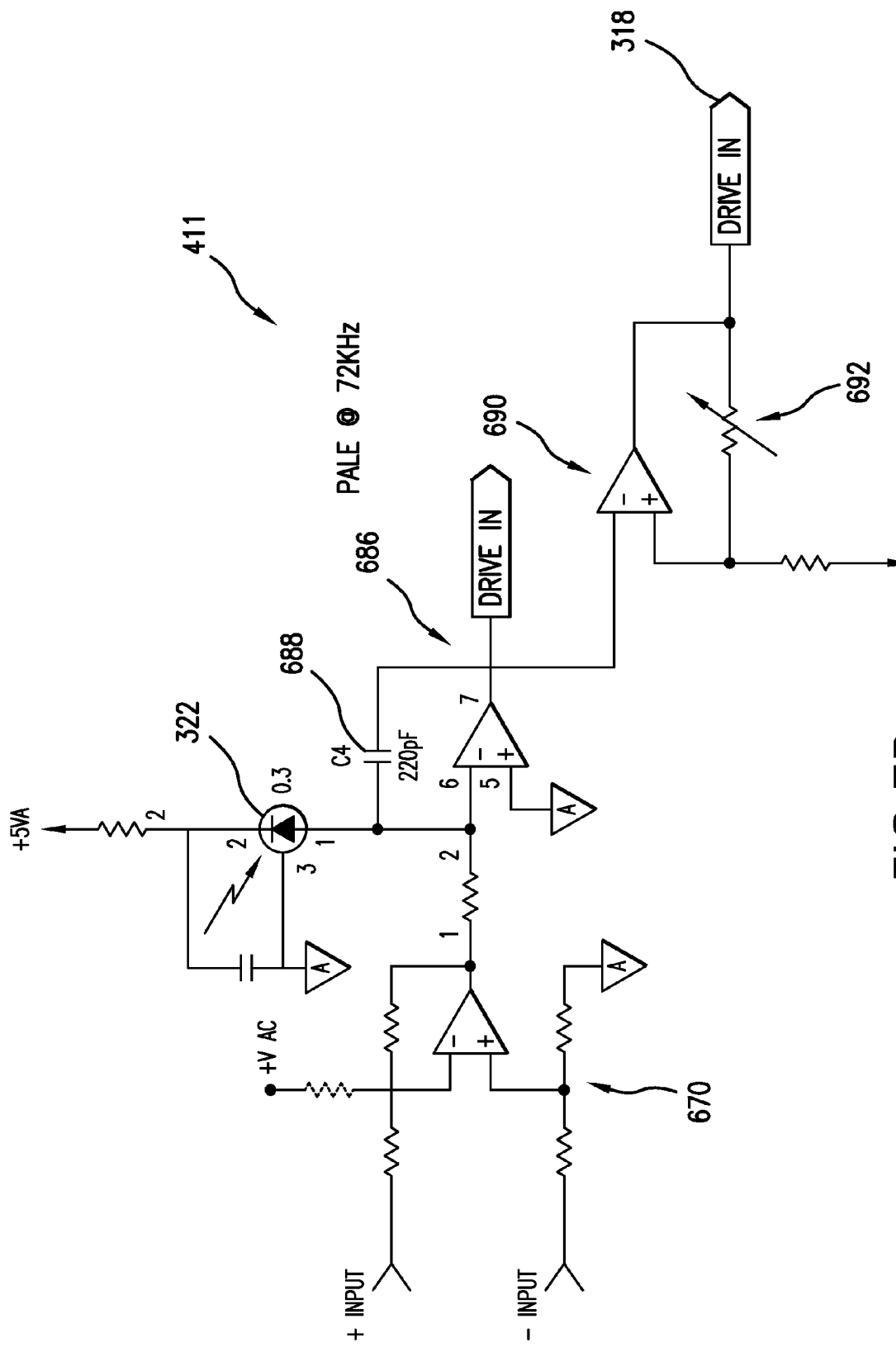
FIG. 7B is a circuit diagram showing an inventive analog drive circuit for the optical modulator.

FIG. 7B is a circuit diagram showing the drive circuit 411 for the modulator/attenuator 318. This circuit similarly has a trans-impedance amplifier 670 to assist in common mode rejection. The power detector photodiode 322 provides the input to an integrating amplifier 686. Capacitor C4 (688) is used to control the loop bandwidth of the amplifier 686. Specifically, by increasing the size of the capacitor C4, the bandwidth is decreased. A second amplifier 690 is used to provide the gain to the input terminal of the attenuator 318. Variable resistor 692 is used to control the gain of the second amplifier 690.

One of the advantages of the present invention is that its optical train can be implemented in a small-robust unit, possibly being integrated on a single optical bench. The following illustrates a number of different embodiments showing various levels of integration.

Figure 8:
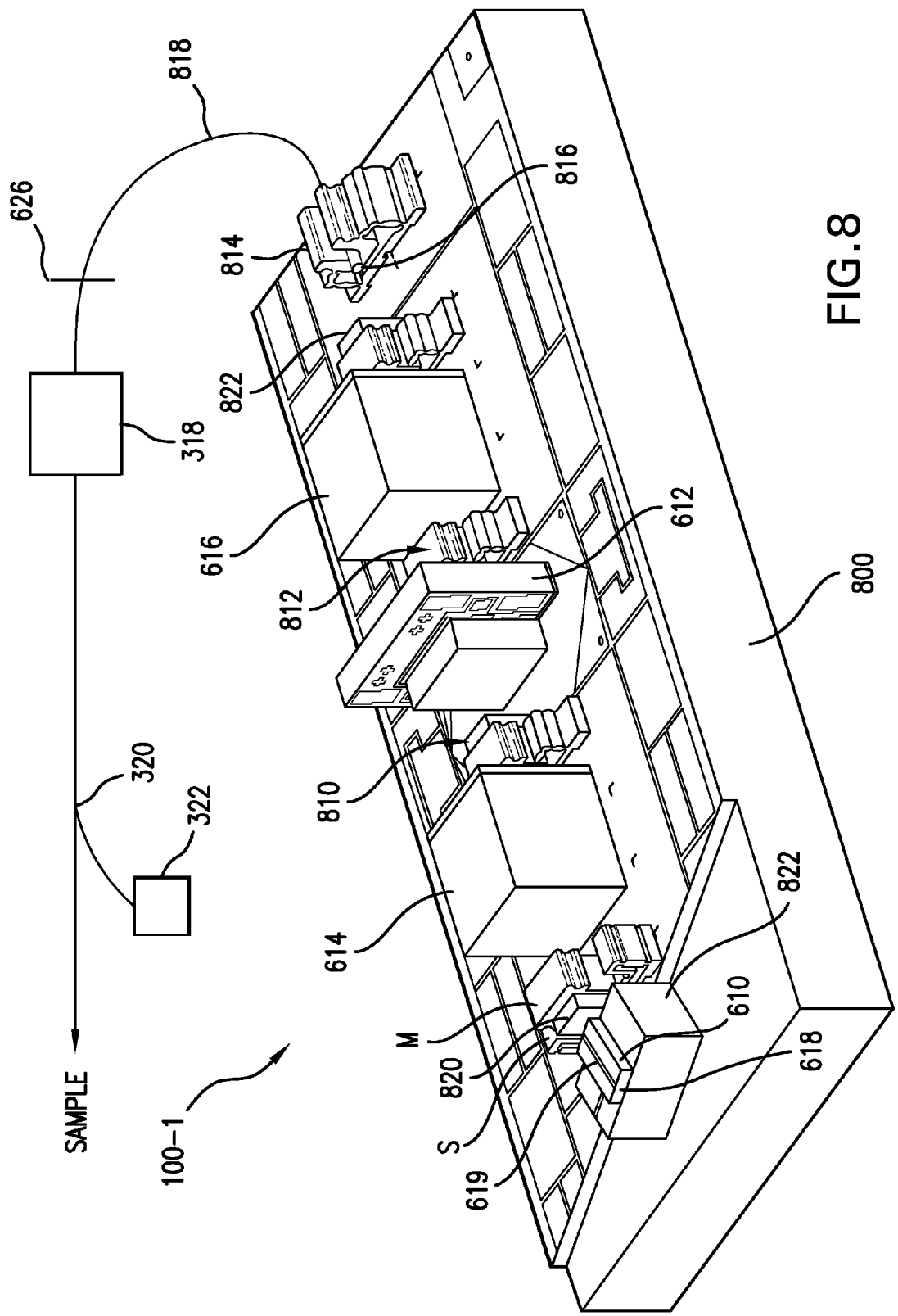
FIG. 8 is a perspective view of a linear cavity tunable laser according to the present invention.

FIG. 8 is a perspective view of one embodiment of the tunable laser linear cavity configuration 200-1 illustrated in block diagram form in FIG. 2A. Specifically, the tunable laser 200-1 is integrated on a common bench 800. Specifically, the SOA chip 610 is installed on a submount 822, which holds the chip 610 off of the bench 800. The back facet 618 of the chip 610 functions as the back reflector 618 of this linear cavity laser.

The chip's waveguide 619 generates light that is collimated by a first lens component 820. Specifically, this lens component comprises a lens substrate S that is installed on the bench 800 via a mounting structure M.

The collimated light from the first lens component 820 passes through a first isolator 614 or quarter waveplate to a second lens component 810. This second lens unit 810 focuses the light to launch it into the MEMS Fabry-Perot tunable filter 612. Light in the passband, exiting from the tunable filter 612, is recollimated by a third lens component 812 to pass through the second isolator 616 to a focusing lens component 822.

An endface 816 of the fiber 818 collects the light. A reflector 626 is provided on the fiber to function as the output end of the laser cavity. This fiber 818 is then fiber coupled to the attenuator 318, if used. A fiber tap 320 directs a portion of the tunable optical signal from the attenuator 318 to the power detector 322.

Note that in other embodiments, the attenuator 318, tap 320, and detector 322 are integrated in common on the bench 800 with the other components of the tunable laser.

FIG. 9 is a perspective view of one embodiment of the tunable laser linear cavity configuration 200-2 illustrated in block diagram form in FIG. 2B. Specifically, the tunable laser 200-2 is integrated on a common bench 800. Specifically, the SOA chip 610 is installed on a submount 822, which holds the chip 610 off of the bench 800. The back facet 618 of the chip 610 functions as the back reflector 618 of this linear cavity laser.

The chip's waveguide 619 generates light that is collimated by a first lens component 820. Specifically, this lens component comprises a lens substrate S that is installed on the bench 800 via a mounting structure M The collimated light from the first lens component 820 is launched into the MEMS Fabry-Perot tunable filter 612. Light in the filter passband, exiting from the tunable filter 612, is recollimated by a third lens component 812 to enter endface 816 of the fiber 818. The filter optical axis is tilted such that reflected light outside the filter passband is not coupled back to the semiconductor chip waveguide. A reflector 626 is provided on the fiber to function as the output end of the laser cavity. This fiber 818 is then fiber coupled to the attenuator 318, if used. A fiber tap 320 directs a portion of the tunable optical signal from the attenuator 318 to the power detector 322.

Note that in other embodiments, the attenuator 318, tap 320, and detector 322 are integrated in common on the bench 800 with the other components of the tunable laser.

Figure 9A:
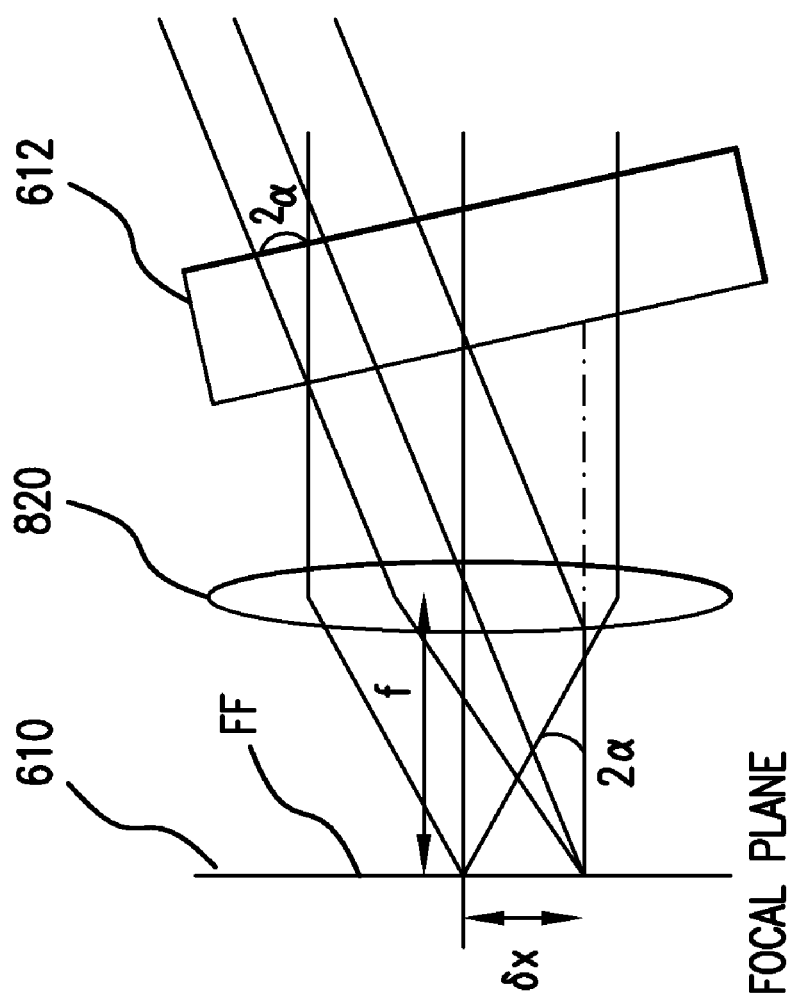
FIG. 9A illustrates the optical train between the SOA chip and the tilted Fabry Perot tunable filter, according to the invention.

FIG. 9A illustrates one embodiment of the optical train between the front facet of the SOA 610 and the tunable filter 612. Specifically, the beam displacement δx enables the decoupling of the back reflection from the filter 612 and the SOA 610. Here is it is less than about 50 micrometers, and preferably less than 20 micrometer, specifically about 10 micrometers. In the example, the distance between the chip front facet ff and the filter 612 is less than about 10 millimeters. The focal length of the first lens component is less than 0.5 millimeters, specifically about 200 micrometers, of specified at 220 micrometers.

Figure 10:
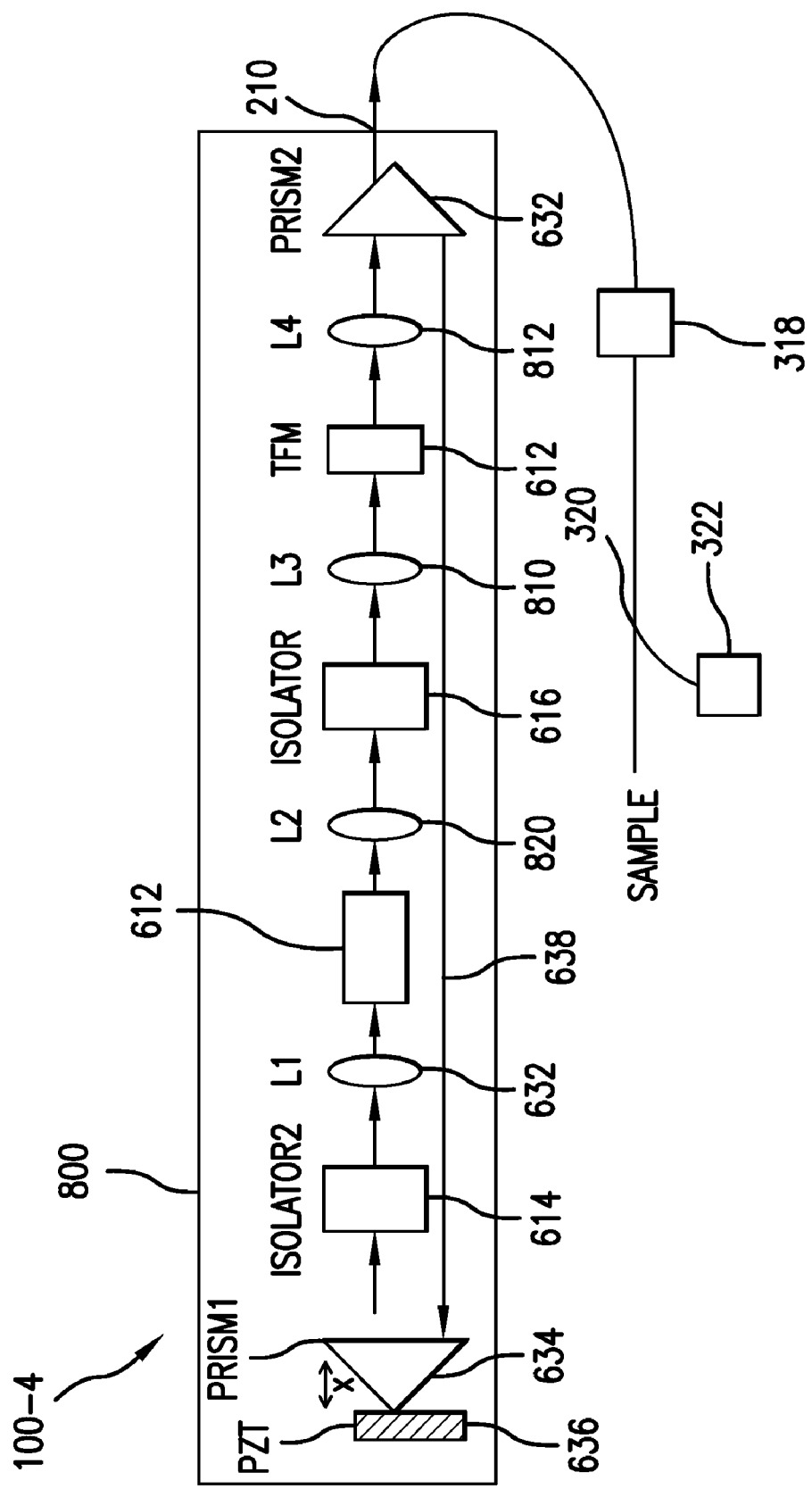
FIG. 10 is a schematic view of a ring cavity tunable laser according o the present invention.

FIG. 10 is a block diagram showing one configuration of the ring laser illustrated in FIG. 2D. Here again, the components are installed on an optical bench 800. Light is generated in the SOA chip 612 and collimated by a first lens 820 to pass through an isolator 616 to a second lens 810 that launches the light into the MEMS Fabry-Perot tunable filter 612. The light exiting from the tunable filter 612 is then recollimated by a third lens 812. A portion of the light exits from the tunable laser cavity as the tunable signal 210. The remaining light, however, is returned to recirculate through the cavity.

In one implementation, this is achieved by a reflector or prism 632 that is attached onto the bench 800. In other implementations, the light is recirculated through the cavity using a length of polarization maintaining (pm) single mode fiber 635. The second embodiment has advantages in that the length of the optical cavity can be controlled. Specifically, the cavity can be made longer to increase the longitudinal modal density.

In any event, the light returns along path 638, which can be above the bench 800 or provided by pm fiber length. Returning light is returned by a prism 634 through a second isolator 614 and a lens 632 to be reamplified in the SOA 612.

In one embodiment, the prism 634 is mounted to the bench 800 using a piezoelectric actuator unit 636. This allows for the location of the prism 634 to be moved in the direction of the X-axis, thereby controlling the length of the optical cavity and therefore the spectral location of the longitudinal modes of the ring laser 100-4.

Figure 11:
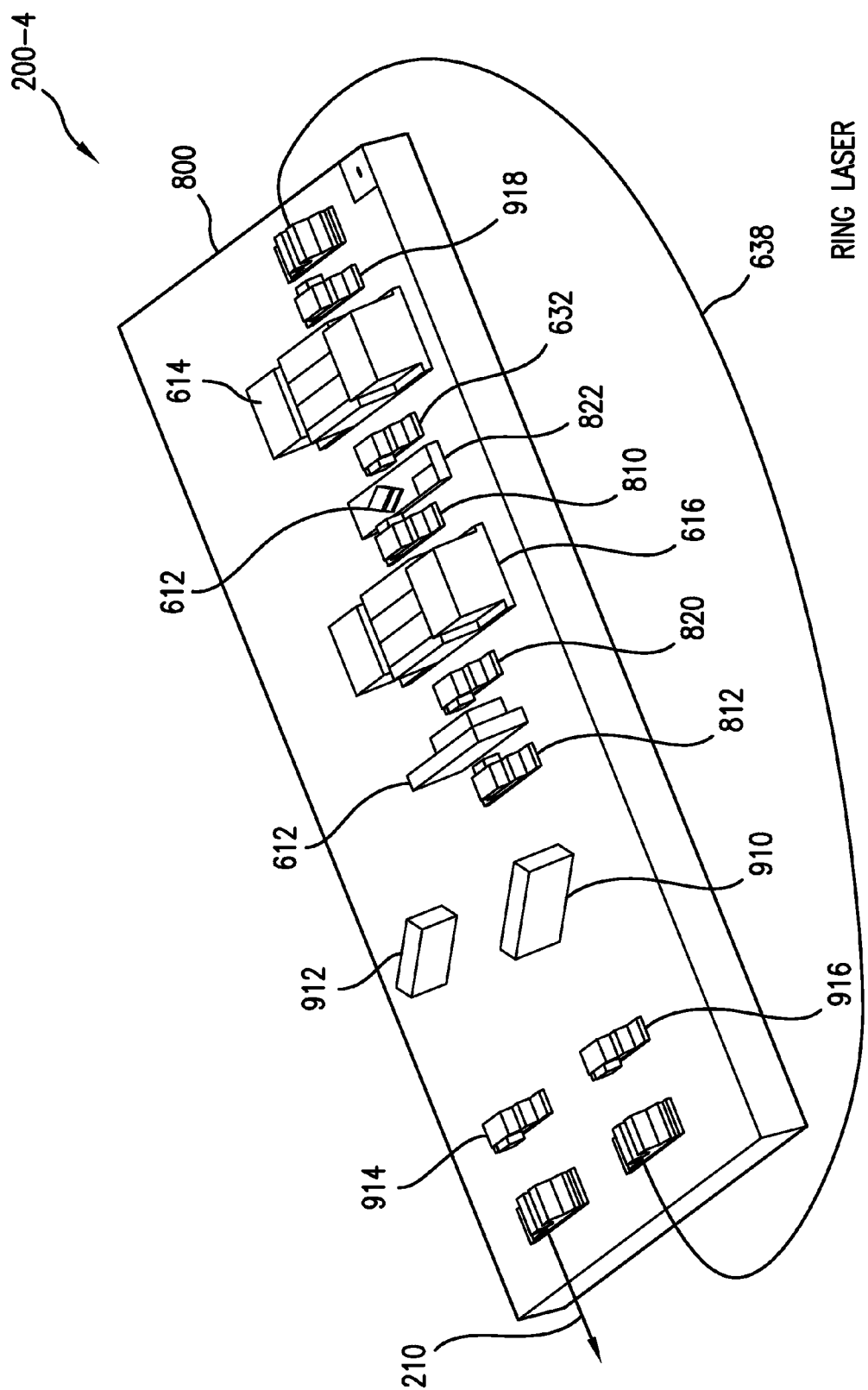
FIG. 11 is a perspective view of the ring cavity tunable laser according o the present invention.

FIG. 11 is a perspective view of the ring laser source 200-4 illustrated in FIG. 2D. The components are installed on optical bench 800. Light is generated in the SOA chip 612 on submount 822. Its light is collimated by a first lens 810 to pass through an isolating device, such as a quarter wave plate 616, to a second lens 820 that launches the light into the MEMS Fabry-Perot tunable filter 612. The light exiting from the tunable filter 612 is then recollimated by a third lens 812. A portion of the light exits from the tunable laser cavity as the tunable signal 210 using tap or splitter 910 and fold mirror 912 and focusing lens 914. The remaining light, however, is returned to recirculate through the cavity via lens 916 and polarization-controlling or pm fiber length 638.

The light returns to lens 918, second isolator 614 and a lens 632 to be reamplified in the SOA 612.

Figure 12:
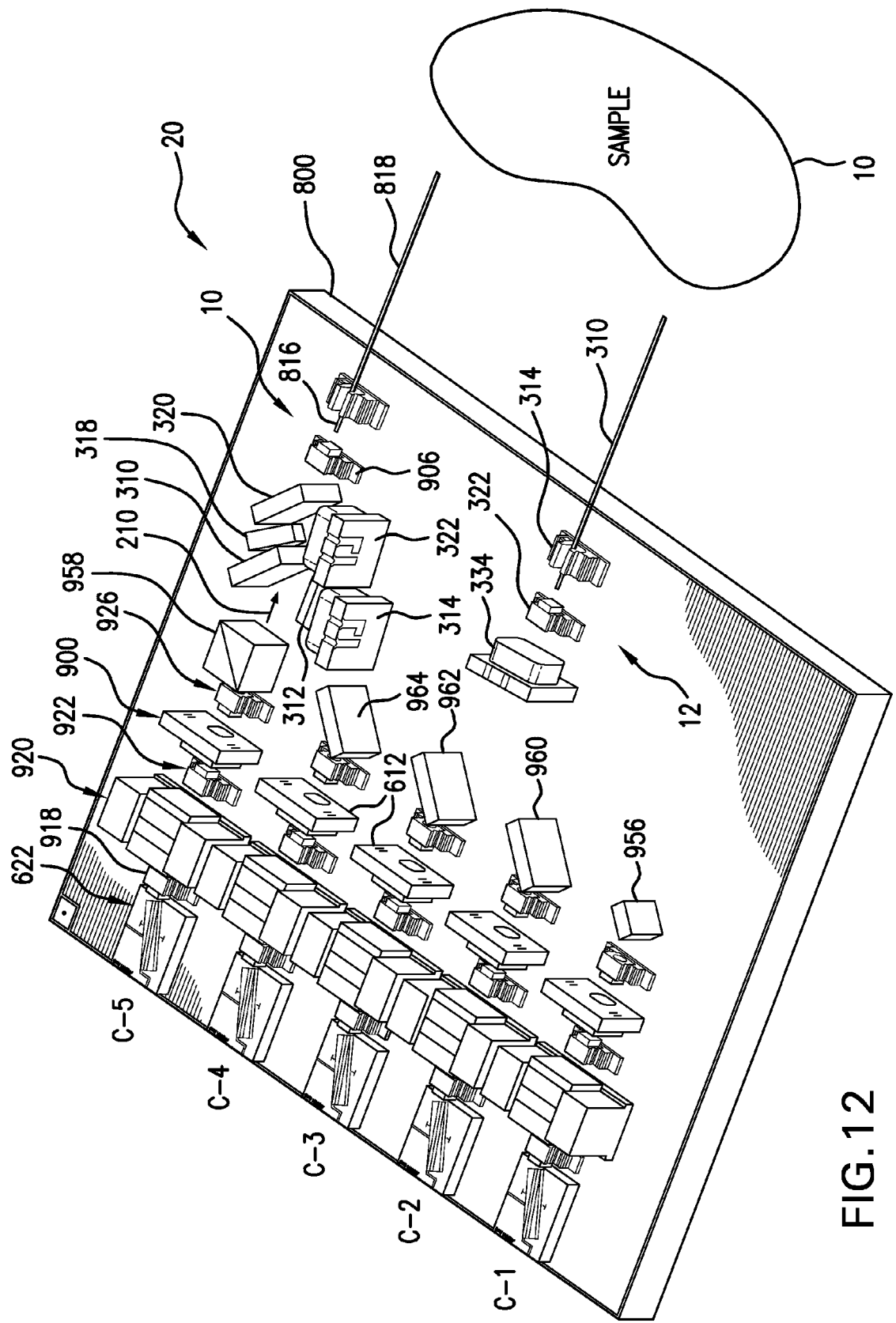
FIG. 12 is a perspective view of a multi-chip tunable SLED system according to the present invention.

FIG. 12 illustrates another embodiment of the tunable source 10, which is based on source 200-3 of FIG. 2C.

This embodiment uses a tunable filter system 900, which includes an array of tunable filters 612 and broadband light sources 622 in order to increase the spectral width of the scanband. Typically, and in the illustrated embodiment, an array of five SLED chips 622 is mounted in common on the bench 800. The light from each of these SLED chips 110 is collimated by respective first lens components 918. Specifically, there is a separate lens component 918 for each of these SLED chips 622. Separate isolators 920 are then provided for the broadband signals from each of the SLED chips 622.

An array of second lens components 922 is further provided to couple the broadband signal into an array 900 of tunable filters 612. Specifically, separate Fabry-Perot tunable filters 612 are used to filter the signal from each of the respective SLED chips 622. Finally, an array of third lens components 926 is used to re-collimate the beam from the tunable Fabry-Perot filters 612 of the tunable filter system 900.

For channel 1, C-1, a fold mirror 956 is used to redirect the beam from the SLED chip 622. The WDM filter 960 is used to combine the broadband signal from the SLED chip 622 of channel C-2 with the signal from channel C-1. Specifically, the filter 960 is reflective to the wavelength range generated by the SLED chip 622 of channel C-2, but transmissive to the wavelength range of light generated by the SLED chip 622 of channel C-1.

WDM filter 962 is reflective to the signal band generated by the SLED chip 622 of channel C-3, but transmissive to the bands generated by SLED chips 622 of channels C-1 and C-2. WDM filter 964 is reflective to the light generated by SLED chip 622 of channel C-4, but transmissive to the bands generated by the SLED chips 622 of channels C-1, C-2, and C-3. Finally, WDM filter 958 is reflective to all of the SLED chips, but the SLED chip 622 of channel C-5. As a result, the light from the array of SLED chips is combined into a single tunable signal 210.

A first tap 310 is provided to reflect a portion of the light through the etalon 312 to be detected by the wavelength detector 314. Then, another portion is reflected by tap 318 to the power detector 322. The remaining tunable signal 210 is coupled by the fourth lens component 906 into the optical fiber 818 via the endface 816.

The FIG. 12 embodiment can operate according to a number of different modes via a controller 410. Specifically, in one example, only one of the SLED chips in channels C-1 to C-5 is operating at any given moment in time. As a result, the tunable signal 210 has only a single spectral peak. The full scan band is achieved by sequentially energizing the SLED chip of each channel C-1 to C-5. This tunable signal is scanned over the entire scan band covered by the SLED chips of channels C-1 to C-5 turning on the SLED chips in series, or sequentially.

In another mode, each of the SLED chips is operated simultaneously. As a result, the tunable signal has spectral peaks in each of the scan bands, covered by each of the SLED chips 622 simultaneously. This system results in a more complex detector system, which must demultiplex the separate scan bands from each of the SLED chips 622 from each of the channels at the detector. Specifically, in one embodiment, five (5) detectors are used with a front-end wavelength demultiplexor.

FIG. 12 further shows a single bench fully integrated system according to still another embodiment. The sample detector system 12 is integrated on the same bench 800 and the tunable source. Specifically, light returning from the sample 10 in fiber 310 is coupled to sample detector chip 334 using lens component 322.

While this invention has been particularly shown and described with references to preferred embodiments thereof, it will be understood by those skilled in the art that various changes in form and details may be made therein without departing from the scope of the invention encompassed by the appended claims.

What is claimed is:

1. A spectroscopy system, comprising
   a tunable laser with a semiconductor source illuminating a sample with a tunable optical signal, which is tunable over a scan band;
   a detector for detecting a sample signal generated by interaction of the tunable optical signal with the sample;
   an optical power control system including:
      an amplitude detector system for detecting an amplitude of the tunable optical signal, located optically between the tunable laser and the sample to detect the tunable signal after generation by the tunable laser and before interaction with the sample, and
      a power control system for regulating the amplitude of the tunable optical signal in response to the detected amplitude by controlling power to the semiconductor source.

2. An optical power control system as claimed in claim 1, wherein the semiconductor source comprises a semiconductor optical amplifier and the laser further comprises a tunable filter that controls the wavelength of the tunable signal.

3. An optical power control system as claimed in claim 2, wherein a laser cavity is a linear cavity.

4. An optical power control system as claimed in claim 2, wherein a laser cavity is a ring cavity.

5. An optical power control system as claimed in claim 2, wherein the tunable filter is a microelectromechanical system filter.

6. An optical power control system as claimed in claim 2, wherein the tunable filter is a microelectromechanical filter comprising thin film coating mirror structures.

7. An optical power control system as claimed in claim 1, wherein the amplitude detector system comprises a detector; and a tap providing a portion of the tunable optical signal to the detector.

8. An optical power control system as claimed in claim 1, wherein semiconductor source spectroscopy system comprises an optical bench, to which the semiconductor source and a tunable filter, controlling the wavelength of the tunable signal, are attached.

9. An optical power control system as claimed in claim 8, wherein the amplitude detector system comprises:
   a detector, which is attached to the bench; and
   a tap, which is attached to the bench, providing a portion of the tunable optical signal to the detector.

10. An optical power control system as claimed in claim 1, wherein the power control system stabilizes the amplitude of the tunable optical signal by controlling power to the semiconductor source.

11. An optical power control system as claimed in claim 1, wherein the power control system comprises an optical signal power regulator for regulating the amplitude of the tunable optical signal.

12. An optical power control system as claimed in claim 1, wherein the power control system comprises an optical signal attenuator for regulating the amplitude of the tunable optical signal by attenuating the tunable optical signal in response to the amplitude detector system.

13. An optical power control method for a spectroscopy system, comprising a laser with a semiconductor source illuminating a sample with a tunable optical signal generated by the laser, which is tunable over a scan band, and a detector for detecting a sample signal generated by interaction of the tunable optical signal with the sample, the optical power control comprising:
   detecting an amplitude of the tunable optical signal after generation by the tunable laser and before interaction with the sample; and
   regulating the amplitude of the tunable optical signal in response to the detected amplitude by controlling power to the semiconductor source.

14. An optical power control method as claimed in claim 13, further comprising a step of generating the tunable optical signal by powering a semiconductor optical amplifier and controlling a wavelength of the tunable optical signal with a tunable filter.

15. An optical power control system as claimed in claim 13, wherein the step of regulating the amplitude comprises regulating the amplitude of the tunable optical signal by attenuating the tunable optical signal in response to the amplitude.

16. A laser system, comprising
a tunable laser with a semiconductor source illuminating a sample with a tunable optical signal, which is tunable over a scan band;
a detector for detecting a sample signal generated by interaction of the tunable optical signal with the sample;
an optical power control system including:
an amplitude detector system for detecting an amplitude of the tunable optical signal, located optically between the tunable laser and the sample to detect the tunable signal after generation by the tunable laser and before interaction with the sample, and
a power control system for regulating the amplitude of the tunable optical signal in response to the detected amplitude by controlling power to the semiconductor source.

17. An optical power control system as claimed in claim 16, wherein the semiconductor source comprises a semiconductor optical amplifier and the laser further comprises a tunable filter that controls the wavelength of the tunable signal.

18. An optical power control system as claimed in claim 16, wherein semiconductor source spectroscopy system comprises an optical bench, to which the semiconductor source and a microelectromechanical tunable filter, controlling the wavelength of the tunable signal, are attached.

19. An optical power control system as claimed in claim 18, wherein the amplitude detector system comprises:
a detector, which is attached to the bench; and
a tap, which is attached to the bench, providing a portion of the tunable optical signal to the detector.

* * * * *